US008541481B2

(12) United States Patent
Determan et al.

(10) Patent No.: US 8,541,481 B2
(45) Date of Patent: Sep. 24, 2013

(54) GENTLE TO SKIN ADHESIVE

(75) Inventors: Michael D. Determan, Woodbury, MN (US); Simon S. Fung, Woodbury, MN (US); Timothy D. Filiatrault, Maplewood, MN (US); Junkang J. Liu, Woodbury, MN (US); Clayton A. George, Afton, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 266 days.

(21) Appl. No.: 13/126,346

(22) PCT Filed: Oct. 29, 2009

(86) PCT No.: PCT/US2009/062603
§ 371 (c)(1),
(2), (4) Date: Apr. 27, 2011

(87) PCT Pub. No.: WO2010/056544
PCT Pub. Date: May 20, 2010

(65) Prior Publication Data
US 2011/0212325 A1    Sep. 1, 2011

Related U.S. Application Data

(66) Substitute for application No. 61/109,213, filed on Oct. 29, 2008.

(60) Provisional application No. 61/109,211, filed on Oct. 29, 2008.

(51) Int. Cl.
*C08F 2/54*    (2006.01)

(52) U.S. Cl.
USPC ............... 522/1; 427/503; 428/447; 525/477

(58) Field of Classification Search
None
See application file for complete search history.

(56) References Cited

U.S. PATENT DOCUMENTS

| | | | |
|---|---|---|---|
| 991,574 A | 5/1911 | Wesson | |
| 2,763,609 A | 9/1956 | Lewis | |
| 2,956,904 A | 10/1960 | Hendricks | |
| 3,146,799 A | 9/1964 | Frank | |
| 4,201,808 A | 5/1980 | Cully | |
| 4,348,454 A | 9/1982 | Eckberg | |
| 4,547,431 A | 10/1985 | Eckberg | |
| 4,684,670 A | 8/1987 | Eckberg | |
| 4,767,494 A | 8/1988 | Kobayashi | |
| 4,810,728 A | 3/1989 | Gross | |
| 4,859,712 A | 8/1989 | Cox | |
| 4,865,920 A | 9/1989 | Sweet | |
| 4,991,574 A | 2/1991 | Pocknell | |
| 5,147,916 A | 9/1992 | Sweet | |
| 5,162,410 A | 11/1992 | Sweet | |
| 5,248,739 A * | 9/1993 | Schmidt et al. | ............... 525/477 |
| 5,302,671 A | 4/1994 | Cifuentes | |
| 5,356,940 A | 10/1994 | Giesen | |
| 5,436,274 A | 7/1995 | Sumpter | |
| 5,543,231 A | 8/1996 | Kidon | |
| 5,661,192 A | 8/1997 | Giraud | |
| 5,670,555 A | 9/1997 | Loiselle | |
| 5,683,527 A | 11/1997 | Angell | |
| 5,747,172 A | 5/1998 | Crivello | |
| 5,753,720 A * | 5/1998 | Nakanishi et al. | ............... 522/33 |
| 5,804,610 A | 9/1998 | Hamer | |
| 5,905,123 A | 5/1999 | Cifuentes | |
| 5,907,018 A | 5/1999 | Mazurek | |
| 5,961,770 A | 10/1999 | Cifuentes | |
| 6,051,747 A | 4/2000 | Lindqvist | |
| 6,207,875 B1 | 3/2001 | Lindqvist | |
| 6,337,086 B1 * | 1/2002 | Kanios et al. | ................. 424/449 |
| 6,359,026 B1 | 3/2002 | Marquardt | |
| 6,406,793 B1 | 6/2002 | Aoki | |
| 6,472,581 B1 | 10/2002 | Muramatsu | |
| 6,545,086 B1 | 4/2003 | Kosal | |
| 6,664,359 B1 | 12/2003 | Kangas | |
| 6,818,673 B2 | 11/2004 | Ferguson | |
| 6,846,508 B1 | 1/2005 | Colas | |
| 6,890,601 B2 | 5/2005 | Griswold | |
| 7,005,475 B2 | 2/2006 | Griswold | |
| 7,371,464 B2 | 5/2008 | Sherman | |
| 7,393,879 B1 | 7/2008 | Kresta | |
| 7,407,709 B2 | 8/2008 | Zhou | |
| 2001/0037008 A1 | 11/2001 | Sherman | |
| 2002/0013442 A1 | 1/2002 | Sherman | |
| 2005/0113479 A1 | 5/2005 | Eckberg | |
| 2005/0136266 A1 | 6/2005 | Zhou | |
| 2005/0282024 A1 | 12/2005 | Sherman | |
| 2007/0110941 A1 | 5/2007 | Utesch | |

(Continued)

FOREIGN PATENT DOCUMENTS

| | | |
|---|---|---|
| EP | 452034 | 10/1991 |
| EP | 2062952 | 5/2009 |

(Continued)

OTHER PUBLICATIONS

Product data sheet for Elastosil LR 3003/20 A and B.*
"Radiation Cross-Linking of Polydimethylsiloxane. Cross-linking and Fracture by Solubility Analysis" authored by Squire et al. and published in Macromolecules (1972) 5(4), 401-404.*
"Silicone Crosslinked by Ionizing Radiation as Potential Polymeric Matrix for Drug Delivery" authored by Rogero et al. and published in Nuclear Instruments and Methods in Physics Research B (2005) 236, 521-525.*
ASTM D 3330M-90 Standard Test Methods for Peel Adhesion of Pressure-Sensitive Tape at 180° Angle [Metric]1, 1990, pp. 464-467.
ASTM E 1818-96[e1], Standard Practice for Dosimetry in an Electron Beam Facility for Radiation Processing at Energies Between 80 and 300 keV[1], 1996, pp. 903-910.
Frounchi,"Comparison Between Electron-beam and Chemical Crosslinking of Silicone Rubber", Nuclear Instruments and Methods in Physics Research B, 2006, vol. 243, pp. 354-358.

(Continued)

*Primary Examiner* — Marc Zimmer
(74) *Attorney, Agent, or Firm* — Trisha D. Adamson (57) ABSTRACT

Electron beam and gamma radiation crosslinked, silicone gel adhesives are described. Both nonfunctional and functional poly diorganosiloxanes are used. Methods of forming the adhesives, and medical articles incorporating such adhesives are also described.

14 Claims, 1 Drawing Sheet

(56) References Cited

U.S. PATENT DOCUMENTS

| | | |
|---|---|---|
| 2007/0202245 A1 | 8/2007 | Gantner |
| 2007/0212314 A1 | 9/2007 | Murphy |
| 2008/0058460 A1 | 3/2008 | Tonge |
| 2009/0117310 A1 | 5/2009 | Ellringmann |
| 2010/0310852 A1 | 12/2010 | Weidinger |
| 2011/0206923 A1 | 8/2011 | Liu |
| 2011/0206924 A1 | 8/2011 | Liu |

FOREIGN PATENT DOCUMENTS

| | | | |
|---|---|---|---|
| GB | 805388 | | 12/1958 |
| GB | 818987 | | 8/1959 |
| JP | 62-149308 | | 7/1987 |
| JP | 5169595 | | 7/1993 |
| JP | 11140323 | | 5/1999 |
| WF | 02-097003 | | 12/2002 |
| WO | 95-23694 | | 9/1995 |
| WO | 96-35458 | | 11/1996 |
| WO | 98-23305 | | 6/1998 |
| WO | WO 98/23305 | * | 6/1998 |
| WO | 99-18166 | | 4/1999 |
| WO | 03-010257 | | 2/2003 |
| WO | 2005-005705 | | 1/2005 |
| WO | WO 2005/063890 | | 7/2005 |
| WO | 2008-027498 | | 3/2008 |
| WO | 2008-057155 | | 5/2008 |
| WO | 2009-076389 | | 6/2009 |
| WO | 2010-056546 | | 5/2010 |
| WO | 2011-136977 | | 11/2011 |

OTHER PUBLICATIONS

Labouriau, "Mössbauer, NMR and ATR-FTIR spectroscopic investigation of degradation in RTV siloxane foams," Polym. Degradation & Stability, 2007, vol. 92, pp. 414-424.

Lin, "Recent advances in silicone pressure-sensitive adhesives," J. Adhesion Sci. Technol., Feb. 2007, vol. 21, No. 7, pp. 605-623.

Park, "Mechanical Properties and Antibacterial Activity of Peroxide-Cured Silicone Rubber Foams," J. Appl. Polym. Sci, May 2008, vol. 110, pp. 1723-1729.

International Search Report for PCT/US2009/062563, Feb. 12, 2010, 3 pages.

International Search Report for PCT/US2009/062576, Feb. 9, 2010, 4 pages.

International Search Report for PCT/US2009/062608, Feb. 8, 2010, 3 pages.

International Search Report for PCT/US2011/033021, mailed Jul. 11, 2011, 3 page.

International Search Report for PCT/US2009/062603, Feb. 9, 2010, 3 pages.

* cited by examiner

GENTLE TO SKIN ADHESIVE

CROSS REFERENCE TO RELATED APPLICATIONS

This application is a national stage filing under 35 U.S.C. 371 of PCT/US2009/062603, filed on Oct. 29, 2009, which claims priority to U.S. Provisional Application Nos. 61/109211 and 61/109213, both filed on Oct. 29, 2008, the disclosure of which are incorporated by reference in their entirety herein.

FIELD

The present disclosure relates to gentle to skin adhesives. Specifically, to silicone gel adhesives and methods of making such adhesives. Such methods include electron beam or gamma ray curing of low molecular weight silicones, including non-functional silicones.

SUMMARY

Briefly, in one aspect, the present disclosure provides an adhesive comprising a radiation cured silicone gel. The silicone gel comprises a crosslinked poly diorganosiloxane material.

In another aspect, the present disclosure provides an adhesive formed by exposing a composition comprising a poly diorganosiloxane material to at least one of electron beam irradiation and gamma irradiation at a sufficient dose to crosslink the poly diorganosiloxane material.

In some embodiments, the poly diorganosiloxane material comprises a poly dimethylsiloxane. In some embodiments, the poly dimethylsiloxane is selected from the group consisting of one or more silanol terminated poly dimethylsiloxanes, one or more non-functional poly dimethylsiloxanes, and combinations thereof. In some embodiments, the poly dimethylsiloxane consists of one or more non-functional poly dimethylsiloxanes.

In some embodiments, the adhesive further comprises a silicate resin tackifier. In some embodiments, the adhesive further comprises a poly(dimethylsiloxane-oxamide) linear copolymer.

In some embodiments, the poly diorganosiloxane material comprises a poly diorganosiloxane fluid having a dynamic viscosity at 25° C. of no greater than 1,000,000 mPa·sec. In some embodiments, the poly diorganosiloxane material consists of poly diorganosiloxane fluids having a kinematic viscosity at 25° C. of no greater than 100,000 centistokes.

In some embodiments, the adhesive has a 180 degree peel adhesion from human skin of no greater than 200 grams per 2.54 centimeters as measured according to the Skin Peel Adhesion Procedure.

In yet another aspect, the present disclosure provides a medical article comprising a layer of any of the silicone adhesives of the present disclosure adhered to a medical substrate. In some embodiments, the layer has a thickness of 20 to 200 microns. In some embodiments, the medical substrate comprises at least one of paper, polymeric film, and woven cloth and non-woven cloth, In a further aspect, the present disclosure provides a method of adhering a medical substrate to a biological substrate. The method comprises adhering an adhesive according to the present disclosure to the medical substrate, and using the adhesive to adhere the medical substrate to the biological substrate. In some embodiments, the biological substrate is human skin.

The above summary of the present disclosure is not intended to describe each embodiment of the present invention. The details of one or more embodiments of the invention are also set forth in the description below. Other features, objects, and advantages of the invention will be apparent from the description and from the claims.

DETAILED DESCRIPTION

The application of pressure sensitive adhesives (PSAs), including silicone pressure sensitive adhesives, for adhering to skin is known in the art and many examples are commercially available. However, some properties of PSAs limit their application for adhesion to skin. For instance, skin damage may result during the removal of a PSA that exhibits too high a level of adhesive strength. Alternatively, if the adhesive strength is reduced, the PSA may lack sufficient holding power to be useful or will lose the room temperature tackiness that makes easy application of the adhesive possible. Additionally PSAs that are relatively rigid or non-conformable compared to skin typically result in considerable patient discomfort during use. Also, even adhesives that have a measured low peel adhesion to skin may cause discomfort during removal, e.g., if the adhesive becomes entangled with hair Silicone gel (crosslinked poly dimethylsiloxane ("PDMS") materials have been used for dielectric fillers, vibration dampers, and medical therapies for promoting scar tissue healing. Lightly crosslinked silicone gels are soft, tacky, elastic materials that have low to moderate adhesive strength compared to traditional, tackified silicone PSAs. Silicone gels are typically softer than silicone PSAs, resulting in less discomfort when adhered to skin. The combination of relatively low adhesive strength and moderate tack make silicone gels suitable for gentle to skin adhesive applications.

Silicone gel adhesives provide good adhesion to skin with gentle removal force and have the ability to be repositioned. Examples of commercially available silicone gel adhesive systems include products marketed with the trade names: Dow Corning MG 7-9850, WACKER 2130, BLUESTAR 4317 and 4320, and NUSIL 6345 and 6350.

These gentle skin adhesives are formed by an addition cure reaction between vinyl-terminated poly(dimethylsiloxane) (PDMS) and hydrogen terminated PDMS, in the presence of a hydrosilation catalyst (e.g., platinum complex). Vinyl-terminated and hydrogen terminated PDMS chains are referred to as 'functionalized' silicones due to their specific chemical moieties. Individually, such functional silicones are generally not reactive; however, together they form a reactive silicone system. Additionally, silicate resins (tackifiers) and PDMS with multiple hydrogen functionalities (crosslinkers) can be formulated to modify the adhesive properties of the gel.

The silicone gel adhesives resulting from the addition cure reaction are very lightly crosslinked polydimethysiloxane (PDMS) networks with some level of free (not crosslinked) PDMS fluid and little or no tackifiying resin. By contrast, tackifying resins are typically used at high levels (45-60 pph) in silicone PSAs.

In addition to the catalyst-promoted curing of silicone materials, it is known that free radicals formed from the high temperature degradation of organic peroxides can crosslink or cure silicone PSA formulations. This curing technique is undesirable due to the acidic residues left in the film from the curing chemistry, which are corrosive and unsuitable for skin contact.

Generally, the crosslinked siloxane networks of the present disclosure can be formed from either functional or non-functional silicone materials. These gel adhesives have excellent wetting characteristics, due to the very low glass transition temperature (Tg) and modulus of the polysiloxane network. Rheologically, these gels exhibit nearly identical storage moduli at bond making and bond breaking time scales, resulting in relatively low to moderate forces being required to debond the adhesive by peeling. This results in minimal to no skin trauma upon removal. Additionally, the elastic nature of the crosslinked gel prevents flow of the adhesive around hair during skin wear, further reducing the instances of pain during removal.

Generally, the silicone materials may be oils, fluids, gums, elastomers, or resins, e.g., friable solid resins. Generally, lower molecular weight, lower viscosity materials are referred to as fluids or oils, while higher molecular weight, higher viscosity materials are referred to as gums; however, there is no sharp distinction between these terms. Elastomers and resins have even higher molecular weights that gums, and typically do not flow. As used herein, the terms "fluid" and "oil" refer to materials having a dynamic viscosity at 25° C. of no greater than 1,000,000 mPa·sec (e.g., less than 600,000 mPa·sec), while materials having a dynamic viscosity at 25° C. of greater than 1,000,000 mPa·sec (e.g., at least 10,000,000 mPa·sec) are referred to as "gums".

Generally, the silicone materials useful in the present disclosure are poly diorganosiloxanes, i.e., materials comprising a polysiloxane backbone. In some embodiments, the non-functionalized silicone materials can be a linear material described by the following formula illustrating a siloxane backbone with aliphatic and/or aromatic substituents:

(1)

wherein R1, R2, R3, and R4 are independently selected from the group consisting of an alkyl group and an aryl group, each R5 is an alkyl group and n and m are integers, and at least one of m or n is not zero. In some embodiments, one or more of the alkyl or aryl groups may contain a halogen substituent, e.g., fluorine. For example, in some embodiments, one or more of the alkyl groups may be —$CH_2CH_2C_4F_9$.

In some embodiments, R5 is a methyl group, i.e., the nonfunctionalized poly diorganosiloxane material is terminated by trimethylsiloxy groups. In some embodiments, R1 and R2 are alkyl groups and n is zero, i.e., the material is a poly (dialkylsiloxane). In some embodiments, the alkyl group is a methyl group, i.e., poly(dimethylsiloxane) ("PDMS"). In some embodiments, R1 is an alkyl group, R2 is an aryl group, and n is zero, i.e., the material is a poly(alkylarylsiloxane). In some embodiments, R1 is methyl group and R2 is a phenyl group, i.e., the material is poly(methylphenylsiloxane). In some embodiments, R1 and R2 are alkyl groups and R3 and R4 are aryl groups, i.e., the material is a poly(dialkyldiarylsiloxane). In some embodiments, R1 and R2 are methyl groups, and R3 and R4 are phenyl groups, i.e., the material is poly(dimethyldiphenylsiloxane).

In some embodiments, the nonfunctionalized poly diorganosiloxane materials may be branched. For example, one or more of the R1, R2, R3, and/or R4 groups may be a linear or branched siloxane with alkyl or aryl (including halogenated alkyl or aryl) substituents and terminal R5 groups.

As used herein, "nonfunctional groups" are either alkyl or aryl groups consisting of carbon, hydrogen, and in some embodiments, halogen (e.g., fluorine) atoms. As used herein, a "nonfunctionalized poly diorganosiloxane material" is one in which the R1, R2, R3, R4, and R5 groups are nonfunctional groups.

Generally, functional silicone systems include specific reactive groups attached to the polysiloxane backbone of the starting material (for example, hydrogen, hydroxyl, vinyl, allyl, or acrylic groups). As used herein, a "functionalized poly diorganosiloxane material" is one in which at least one of the R-groups of Formula 2 is a functional group.

(2)

In some embodiments, a functional poly diorganosiloxane material is one is which at least 2 of the R-groups are functional groups. Generally, the R-groups of Formula 2 may be independently selected. In some embodiments, at least one functional group is selected from the group consisting of a hydride group, a hydroxy group, an alkoxy group, a vinyl group, an epoxy group, and an acrylate group.

In addition to functional R-groups, the R-groups may be nonfunctional groups, e.g., alkyl or aryl groups, including halogenated (e.g., fluorinated) alky and aryl groups. In some embodiments, the functionalized poly diorganosiloxane materials may be branched. For example, one or more of the R groups may be a linear or branched siloxane with functional and/or non-functional substituents.

The gentle to skin adhesives of the present disclosure may be prepared by combining one or more poly diorganosiloxane materials (e.g., silicone oils or fluids), optionally with an appropriate tackifying resin, coating the resulting combination, and curing using electron beam (E-beam) or gamma irradiation. Generally, any known additives useful in the formulation of adhesives may also be included.

If included, generally, any known tackifying resin may be used, e.g., in some embodiments, silicate tackifying resins may be used. In some exemplary adhesive compositions, a plurality of silicate tackifying resins can be used to achieve desired performance.

Suitable silicate tackifying resins include those resins composed of the following structural units M (i.e., monovalent R'$_3$SiO$_{1/2}$ units), D (i.e., divalent R'$_2$SiO$_{2/2}$ units), T (i.e., trivalent R'SiO$_{3/2}$ units), and Q (i.e., quaternary SiO$_{4/2}$ units), and combinations thereof. Typical exemplary silicate resins include MQ silicate tackifying resins, MQD silicate tackifying resins, and MQT silicate tackifying resins. These silicate tackifying resins usually have a number average molecular weight in the range of 100 to 50,000-gm/mole, e.g., 500 to 15,000 gm/mole and generally R' groups are methyl groups.

MQ silicate tackifying resins are copolymeric resins where each M unit is bonded to a Q unit, and each Q unit is bonded to at least one other Q unit. Some of the Q units are bonded to only other Q units. However, some Q units are bonded to hydroxyl radicals resulting in HOSiO$_{3/2}$ units (i.e., "T$^{OH}$"

units), thereby accounting for some silicon-bonded hydroxyl content of the silicate tackifying resin.

The level of silicon bonded hydroxyl groups (i.e., silanol) on the MQ resin may be reduced to no greater than 1.5 weight percent, no greater than 1.2 weight percent, no greater than 1.0 weight percent, or no greater than 0.8 weight percent based on the weight of the silicate tackifying resin. This may be accomplished, for example, by reacting hexamethyldisilazane with the silicate tackifying resin. Such a reaction may be catalyzed, for example, with trifluoroacetic acid. Alternatively, trimethylchlorosilane or trimethylsilylacetamide may be reacted with the silicate tackifying resin, a catalyst not being necessary in this case.

MQD silicone tackifying resins are terpolymers having M, Q and D units. In some embodiments, some of the methyl R' groups of the D units can be replaced with vinyl ($CH_2=CH—$) groups ("$D^{Vi}$" units). MQT silicate tackifying resins are terpolymers having M, Q and T units.

Suitable silicate tackifying resins are commercially available from sources such as Dow Corning (e.g., DC2-7066), Momentive Performance Materials (e.g., SR545 and SR1000), and Wacker Chemie AG (e.g., BELSIL TMS-803).

The polsiloxane material, the tackifying resin, if present, and any optional additives may be combined by any of a wide variety of known means prior to being coated and cured. For example, in some embodiments, the various components may be pre-blended using common equipment such as mixers, blenders, mills, extruders, and the like.

In some embodiments, the materials may be dissolved in a solvent, coated, and dried prior to curing. In some embodiments, solventless compounding and coating processes may be used. In some embodiments, solventless coating may occur at about room temperature. For example, in some embodiments, the materials may have kinematic viscosity of no greater than 100,000 centistokes (cSt), e.g., no greater than 50,000 cSt. However, in some embodiments, hot melt coating processes such as extrusion may be used, e.g., to reduce the viscosity of higher molecular weight materials to values more suitable for coating. The various components may be added together, in various combinations or individually, through one or more separate ports of an extruder, blended (e.g., melt mixed) within the extruder, and extruded to form the hot melt coated composition.

Regardless of how it is formed, the coated compositions are radiation cured. In some embodiments, coating may be cured through exposure to E-beam irradiation. In some embodiments, the coating may be cured through exposure to gamma irradiation. In some embodiments, a combination of electron beam curing and gamma ray curing may be used. For example, in some embodiments, the coating may be partially cured by exposure to electron beam irradiation. Subsequently, the coating may be further cured by gamma irradiation.

A variety of procedures for E-beam and gamma ray curing are well-known. The cure depends on the specific equipment used, and those skilled in the art can define a dose calibration model for the specific equipment, geometry, and line speed, as well as other well understood process parameters.

Commercially available electron beam generating equipment is readily available. For the examples described herein, the radiation processing was performed on a Model CB-300 electron beam generating apparatus (available from Energy Sciences, Inc. (Wilmington, Mass.). Generally, a support film (e.g., polyester terephthalate support film) runs through a chamber. In some embodiments, a sample of uncured material with a liner (e.g., a fluorosilicone release liner) on both sides ("closed face") may be attached to the support film and conveyed at a fixed speed of about 6.1 meters/min (20 feet/min). In some embodiments, a sample of the uncured material may be applied to one liner, with no liner on the opposite surface ("open face"). Generally, the chamber is inerted (e.g., the oxygen-containing room air is replaced with an inert gas, e.g., nitrogen) while the samples are e-beam cured, particularly when open-face curing.

The uncured material may be exposed to E-beam irradiation from one side through the release liner. For making a single layer laminating adhesive type tape, a single pass through the electron beam may be sufficient. Thicker samples, may exhibit a cure gradient through the cross section of the adhesive so that it may be desirable to expose the uncured material to electron beam radiation from both sides.

Commercially available gamma irradiation equipment includes equipment often used for gamma irradiation sterilization of products for medical applications. In some embodiments, such equipment may be used to cure, or partially cure the gentle to skin adhesives of the present disclosure. In some embodiments, such curing may occur simultaneously with a sterilization process for a semi-finished or finished product, for example a tape or wound dressing.

In some embodiments, the gentle to skin adhesives of the present disclosure are suitable for forming medical articles such as tapes, wound dressings, surgical drapes, IV site dressings, a prosthesis, an ostomy or stoma pouch, a buccal patch, or a transdermal patch. In some embodiments, the adhesives may also be useful for other medical articles including dentures and hairpieces.

In some embodiments, the adhesives may include any of a variety of known fillers and additives including, but not limited to, tackifiers (e.g., MQ resins), fillers pigments, additives for improving adhesion, additives for improving moisture-vapor transmission rate, pharmaceutical agents, cosmetic agents, natural extracts, silicone waxes, silicone polyethers, hydrophilic polymers and rheology modifiers. Additives used to improve adhesion, particularly to wet surfaces, include polymers such as poly(ethylene oxide) polymers, poly(propylene oxide) polymers and copolymers of poly(ethylene oxide and propylene oxide), acrylic acid polymers, hydroxyethyl cellulose polymers, silicone polyether copolymers, such as copolymers of poly(ethylene oxide) and polydiorganosiloxane and copolymers of poly(propylene oxide) and polydiorganosiloxane, and blends thereof.

In some embodiments, the gentle to skin adhesives of the present disclosure are suitable for adhering a medical substrate to a biological substrate (e.g., a human or an animal). For example, in some embodiments, the gentle to skin adhesives of the present disclosure may be used to adhere medical substrates to the skin of humans and/or animals.

Exemplary medical substrates include polymeric materials, plastics, natural macromolecular materials (e.g., collagen, wood, cork, and leather), paper, woven cloth and nonwoven cloth, metals, glass, ceramics, and composites.

The thickness of the adhesive layer is not particularly limited. In some embodiments, the thickness will be at least 10 microns, and in some embodiments, at least 20 microns. In some embodiments, the thickness will be no greater than 400 microns, and in some embodiments, no greater than 200 microns.

The peel adhesion to biological substrates such as human skin is known to be highly variable. Skin type, location on the body, and other factors can affect results. Generally, average values of peel adhesion from skin are subject to large standard deviations. In some embodiments, the average peel adhesion for human skin may be less than 200 gm/2.54 cm, and in some embodiments, less than 100 gm/2.54 cm.

Figure 1:
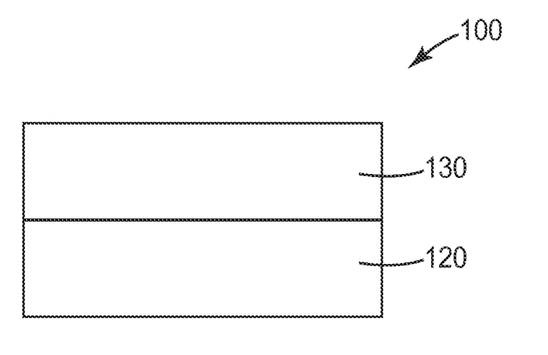
FIG. 1 illustrates a medical article according to some embodiments of the present disclosure.

Exemplary medical article 100 is illustrated in FIG. 1. Medical article 100 comprises silicone adhesive 130 associated with a first major surface of substrate 120. Although not shown, in some embodiments, the opposite surface adhesive 130 may be protected by a release liner. In some embodiments, medical article 100 may be self wound, and the opposite (exposed) surface of the adhesive will come into contact with the uncoated major surface of substrate 120. In use, the surface of the adhesive is applied to the biological substrate, e.g., human skin, adhering substrate 120 to the biological substrate.

EXAMPLES

E-Beam Curing Procedure. E-beam curing was performed on a Model CB-300 electron beam generating apparatus (available from Energy Sciences, Inc. (Wilmington, Mass.). Generally, a support film (e.g., polyester terephthalate support film) was run through the inerted chamber of the apparatus. Samples of uncured material were attached to the support film and conveyed at a fixed speed of about 6.1 meters/min (20 feet/min) through the inerted chamber and exposed to electron beam irradiation.

Gamma Beam Curing Process. The irradiation with gamma rays was accomplished using a source strength of 1.5 to 3 million curie (MCi) consisting of a series of hollow stainless steel tubes containing cobolt-60 (Co-60). Generally, mid-way through the dose exposure of multiple samples, the samples were retrieved from the irradiation chamber, and their relative positions reversed to provide a more uniform exposure. The samples were conveyed into the irradiation chamber and exposed to gamma rays for periods of time necessary to achieve the desired dose. Total absorbed doses ranged from 0.2 to 3 Mrad (2 to 30 kGy) and dose rates were about 0.3 to 0.5 Mrad/hour (3 to 5 kGy/hour).

Peel Test Procedure. Peel adhesion was measured using an IMass 2000 peel tester. The adhesive sample was slit to a width of 1.3 cm (0.5 in.) and length of 12.7 cm (5 in.). The resulting tape was then applied to a clean polypropylene panel (obtained from Standard Plaque Inc. (Melvindale, Mich.)) using four total passes of a 2 kg (4.5 lb) hard rubber roller. The sample was aged before testing for 20 minutes at room temperature (22° C.) and 50% relative humidity. The panel was then mounted on the bed of the IMass 2000 Tester and the tape was pulled off at a 180 degree angle at a speed of 30.5 cm/minute (12 in/min). Results were measured in grams force per 0.5 inch, and converted to g/2.54 cm.

Tack Test Procedure. Tack was measured using a TA-XT Plus Texture Analyzer equipped with a 6 mm diameter polypropylene cylinder probe. The adhesive sample was slit to a width of 1.9 cm (0.75 in.) and length of 10.2 cm (4 in.) and laminated to a brass bar with 10 mm diameter holes through it to allow for the probe to reach the adhesive face of the tape. Test parameters were: Pretest: 0.5 mm/sec, test speed: 1.0 mm/sec, pretest speed: 10.0 mm/sec, applied force: 100 grams, contact time: 5 seconds, trigger force: 1 gram, and withdraw distance: 3 mm.

Skin Peel Adhesion Procedure. Four male and two female subjects were enrolled into this study. The backs of all subjects were washed using IVORY SOAP prior to sample application. The adhesive samples were slit to a width of 2.54 cm (1.0 in.) and length of 7.62 cm (3 in.) Samples were placed on the subject's back positioned so that the long axis of each sample was oriented perpendicular to the volunteer's spine. The order of application of sample materials was randomized (i.e. rotational placement) on each subject. Sample materials were secured using a 2 kg. (4.5-pound) roller of 3M design. The samples were removed at 180 degrees at a rate of 30.5 cm/minute (12 inches per minute). The peel force was measured with a load cell in units of grams force. An initial set of adhesive materials were applied and immediately removed ("T-0"). An additional set of samples were applied and allowed to dwell for 72 hours before removal ("T-72").

The materials used in the following examples are summarized in Table 1.

TABLE 1

Summary of materials.

| Material | Description | Source |
| --- | --- | --- |
| TMS-803 | MQ-tackifying resin | Wacker Chemie AG |
| EL Polymer NA | PDMS gum (a) | Wacker Chemie AG |
| DC-200-A | Dow Corning 200 PDMS fluid (5000 cSt) | Dow Corning, Midland, MI |
| DC-200-B | Dow Corning 200 PDMS fluid (12,500 cSt) | Dow Corning, Midland, MI |
| DMS-S42 | Silanol functional PDMS fluid (18,000 cSt) | Gelest, Inc. |
| OHX-4070 | Terminal silanol functional PDMS fluid (50,000 cSt) | XIAMETER, Midland, MI |
| SPOx | poly(dimethylsiloxane-oxamide) linear copolymer | Prepared as described below |

(a) No reported kinematic viscosity, but this material was a highly viscous gum.

Preparation of SPOx. a Silicone Polyoxamide (SPOx) Elastomer was Prepared in two steps. In the first step, an α,ω-bis(aminopropyl) polydimethylsiloxane diamine with a molecular weight of 25,000 grams/mole was capped with diethyloxalate to provide a α,ω-oxamido oxalate ester capped precursor. (α is the Greek letter alpha, and ω is the Greek letter omega.) This step was completed by following the general procedure of Preparative Example 1 in U.S. Pat. No. 7,371,464. The diethyloxalate is used in a molar excess to the diamine to provide the α,ω-oxamido oxalate ester capped precursor. This precursor was chain-extended into the silicone polyoxamide elastomer using ethylenediamine following general procedure of Example 3 in U.S. Pat. No. 7,371,464 with the exception that only the precursor prepared above was used instead a mixture of precursors and the reaction time was four days. The mole ratio of precursor to ethylenediamine was 1 to 1. The material was used neat without determining the hardness.

Examples 1-12. Solvent-based coatings were prepared from high molecular weight silicone gum. The components of Examples 1-12, shown in Table 2A, were dissolved in toluene at 25 weight % total solids to yield homogeneous solutions. These solutions were coated on a SCOTCHPAR PET film (51 micron polyethylene terephthalate film from 3M Company) using a knife coater. The toluene was removed by placing the coating in a drying oven maintained at 70° C. for 10 minutes. The dry thickness of the adhesives in Examples 1-12 was 51 microns (2 mils). The samples were laminated with the SIL-FLU M50 MD07 release liner (obtained from Siliconature, Inc., Venice, Italy).

TABLE 2A

Composition of Examples 1-12.

| | Parts by weight | | | |
| --- | --- | --- | --- | --- |
| EX. | EL Polymer NA | SPOx Elastomer | DC-200-A PDMS fluid | TMS-803 MQ tackifier |
| 1 | 40 | 20 | 40 | 0 |
| 2 | 57.5 | 7.5 | 30 | 5 |

TABLE 2A-continued

Composition of Examples 1-12.

| EX. | Parts by weight | | | |
|---|---|---|---|---|
| | EL Polymer NA | SPOx Elastomer | DC-200-A PDMS fluid | TMS-803 MQ tackifier |
| 3 | 42.5 | 12.5 | 30 | 15 |
| 4 | 70 | 0 | 30 | 0 |
| 5 | 70 | 0 | 25 | 5 |
| 6 | 70 | 0 | 10 | 20 |
| 7 | 60 | 0 | 40 | 0 |
| 8 | 60 | 0 | 35 | 5 |
| 9 | 60 | 0 | 15 | 25 |
| 10 | 50 | 0 | 35 | 15 |
| 11 | 50 | 0 | 25 | 25 |
| 12 | 50 | 0 | 15 | 35 |

These samples were then irradiated with either electron beam radiation at an acceleration voltage of 220 keV, or gamma radiation as denoted in Table 2B. The peel adhesion and probe tack properties were measured and are also reported in Table 2B.

TABLE 2B

Properties of cured samples of Examples 1-12.

| EX. | Radiation | Dose (Mrad) | Peel Force (g/2.54 cm) | Comments | Probe Tack (g) |
|---|---|---|---|---|---|
| 1 | E-Beam | 2 | 10 | clean peel | 119 |
| | | 2.5 | 8 | clean peel | 89 |
| 2 | E-Beam | 2 | 49 | clean peel | 128 |
| | | 2.5 | 24 | clean peel | 91 |
| 3 | E-Beam | 2 | 85 | clean peel | 119 |
| | | 2.5 | 72 | clean peel | 115 |
| 4 | E-Beam | 2 | 8 | clean peel | 126 |
| | | 2.5 | 7 | clean peel | 64 |
| 5 | E-Beam | 2 | 21 | clean peel | 131 |
| | | 2.5 | 23 | clean peel | 129 |
| 6 | E-Beam | 2 | 73 | clean peel | 142 |
| | | 2.5 | 103 | clean peel | 104 |
| 7 | E-Beam | 2 | 8 | clean peel | 114 |
| | | 2.5 | 16 | clean peel | 86 |
| 8 | E-Beam | 2 | 31 | clean peel | 192 |
| | | 2.5 | 101 | clean peel | 151 |
| 9 | E-Beam | 2 | 114 | clean peel | 143 |
| | | 2.5 | 66 | clean peel | 142 |
| | Gamma | 0.2 | — | cohesive split | — |
| | | 2.5 | 11 | clean peel | 84 |
| | | 3 | 11 | clean peel | 81 |
| 10 | E-Beam | 2 | 60 | clean peel | 180 |
| | | 2.5 | 91 | clean peel | 160 |
| | Gamma | 0.2 | — | cohesive split | — |
| | | 2.5 | 18 | clean peel | 87 |
| | | 3 | 14 | clean peel | 91 |
| 11 | E-Beam | 2 | 91 | clean peel | 170 |
| | | 2.5 | 108 | clean peel | 190 |
| | Gamma | 0.2 | — | cohesive split | — |
| | | 2.5 | 15 | clean peel | 101 |
| | | 3 | 14 | clean peel | 88 |
| 12 | E-Beam | 2 | 94 | clean peel | 165 |
| | | 2.5 | 168 | clean peel | 200 |
| | Gamma | 0.2 | — | cohesive split | — |
| | | 2.5 | 24 | clean peel | 142 |
| | | 3 | 54 | clean peel | 103 |

Examples 13-16. Solventless coatings were prepared from low molecular weight silicone oils or fluids, including a terminal silanol functional PDMS. Although the coatings included a functional PDMS, they were not typical of commercial reactive silicone systems. In particular, as the coating did not contain any materials having functional groups reactive with the terminal silanol groups, no chemical crosslinking would occur with the systems of Examples 13-16.

The formulation components of Examples 13-16, shown in Table 3A, were added to a jar and allowed to mix for at least 48 hours to produce a homogeneous solution. These solutions were coated on SCOTCHPAK PET film using a knife coater to yield 150 micron (6 mil) thick films. These samples were irradiated with electron beam radiation using an acceleration voltage of 280 keV. The electron beam dose and the measured peel adhesion and probe tack properties are reported in Table 3B.

TABLE 3A

Composition of Examples 13-16.

| EX. | Parts by weight | | |
|---|---|---|---|
| | DMS S42 PDMS fluid | DC-200-B PDMS fluid | TMS-803 MQ tackifier |
| 13 | 100 | 0 | 0 |
| 14 | 95 | 0 | 5 |
| 15 | 45 | 50 | 5 |
| 16 | 28 | 67 | 5 |

TABLE 3B

Properties of electron beam cured samples of Examples 13-16.

| EX. | Radiation | Dose (Mrad) | Peel Force (g/2.54 cm) | Comments | Probe Tack (g) |
|---|---|---|---|---|---|
| 13 | E-Beam | 7 | 26 | clean peel | 118 |
| | | 8 | 6 | clean peel | 70 |
| 14 | E-Beam | 6 | 87 | clean peel | 194 |
| | | 7 | 60 | clean peel | 207 |
| 15 | E-Beam | 8 | 53 | clean peel | 173 |
| | | 9 | 33 | clean peel | 190 |
| 16 | E-Beam | 9 | 53 | clean peel | 164 |
| | | 10 | 18 | clean peel | 181 |

Examples 17-21. Solventless coatings were prepared from low molecular weight silicone oils or fluids. These coatings included only non-functional PDMS. The formulation components of Examples 17 through 21, shown in Table 4A, were added to a jar and allowed to mix for at least 48 hours to produce a homogeneous solution. These solutions were coated on SCOTCHPAK PET film using a knife coater to yield 150 micron (6 mil) thick films. These samples were irradiated with electron beam radiation using an acceleration voltage of 280 keV. The electron beam dose and the measured peel adhesion and probe tack properties are reported in Table 4B.

TABLE 4A

Composition of Examples 17-21.

| EX. | Parts by weight | | |
|---|---|---|---|
| | DC-200-B (12,500 cSt PDMS fluid) | DC-200-A (5000 cSt PDMS fluid) | TMS-803 MQ tackifier |
| 17 | 100 | 0 | 0 |
| 18 | 98 | 0 | 2 |
| 19 | 95 | 0 | 5 |
| 20 | 91 | 0 | 9 |
| 21 | 64 | 31 | 5 |

TABLE 4B

Properties of cured samples of Examples 17-21.

| EX. | Radiation | Dose (Mrad) | Peel Force (g/2.54 cm) | Probe Tack (g) |
|---|---|---|---|---|
| 17 | E-Beam | 7 | 22 | 146 |
| 18 | E-Beam | 7 | 40 | 207 |
| 19 | E-Beam | 7 | 48 | 191 |
| 20 | E-Beam | 7 | 58 | 199 |
| 21 | E-Beam | 7 | 47 | 174 |

Examples 22-24. The formulation components of Examples 22 through 24, shown in Table 5A, were added to a jar and allowed to mix for at least 48 hours to produce a homogeneous solution.

TABLE 5A

Composition of Examples 22-24.

| | Parts by weight | | |
|---|---|---|---|
| EX. | OHX-4070 Terminal silanol functional PDMS fluid (50,000 cSt)) | TMS-803 MQ tackifier | Parts by wt. tackifer per 100 parts PDMS fluid |
| 22 | 87 | 13 | 10 |
| 23 | 77 | 23 | 15 |
| 24 | 69 | 31 | 20 |

These solutions were coated on a film consisting of a polyester/cellulose acetate woven fabric that has been heat laminated to a 25 micron (1 mil) Hytrel™ film. The coating was applied using a knife coater to yield films of various thicknesses. These samples were irradiated with electron beam radiation using an acceleration voltage of 280 keV. The peel adhesions from a propylene panel and from human skin were tested and the results are reported in Table 5B, along with the electron beam dose. Due the high variability associated with testing on human skin, the standard deviation (std.) for the peel from skin is also reported.

TABLE 5B

Properties of cured samples of Examples 22-24.

| | | | | | 180 degree peel adhesion (g/2.54 cm) | | | |
|---|---|---|---|---|---|---|---|---|
| EX. | Radiation | Adhesive thickness (microns) | E-beam Dose (Mrad) | Polypropylene panel | Human skin (T-0) Avg. | std. | Human skin (T-72) Avg. | std. |
| 22 | E-Beam | 130 (5 mils) | 7 | 58 | 60 | 15 | 42 | 24 |
| | | 180 (7 mils) | 7 | 65 | 62 | 11 | 57 | 20 |
| 23 | E-Beam | 75 (3 mils) | 8 | 50 | 60 | 7 | 52 | 15 |
| | | 130 (5 mils) | 8 | 75 | 66 | 12 | 54 | 21 |
| | | 180 (7 mils) | 8 | 81 | 76 | 8 | 64 | 22 |
| 24 | E-Beam | 130 (5 mils) | 8.5 | 79 | 83 | 12 | 63 | 25 |
| | | 180 (7 mils) | 8.5 | 102 | 96 | 21 | 66 | 33 |

For comparison, the T-0 and T-72 180 degree peel adhesions to skin for two commercially available medical adhesive products were tested. MEPITAC soft silicone dressing tape (available from Molnlycke Health Care) had a T-0 peel adhesion to human skin of 68 (+/−12) grams per 2.54 cm, and a T-72 peel adhesion to human skin of 58 (+/−23) grams per 2.54 cm. MICROPORE surgical tape (available from 3M Company) had a T-0 peel adhesion to human skin of 65 (+/−44) grams per 2.54 cm, and a T-72 peel adhesion to human skin of 145 (+/−46) grams per 2.54 cm.

In some embodiments, the silicone gel adhesives of the present disclosure are particularly suitable for adhesion to skin. Generally, the adhesives of the present disclosure have a lower surface tension than skin, therefore allowing the adhesive to wet quickly and extensively. The gel adhesive also spread under low deformation rate when enhanced by light pressure and have viscoelastic properties such that they deliver the desired level of adhesion in terms of intensity and duration.

The adhesives are cross-linked poly dimethylsiloxanes and their properties are mainly based on the ability of the surface to quickly wet the substrate and conform to it without excessive flow. Only small dissipation of energy occurs when deformation pressure is applied. The advantage of such adhesives is atraumatic removal, e.g., no skin stripping and no painful pulling of hair or skin. Another property is that the adhesives have a low viscous component that limits their flow and the attachment of epithelial cells, hence it can be removed and adhered easily to the same or other skin surface.

Various modifications and alterations of this invention will become apparent to those skilled in the art without departing from the scope and spirit of this invention.

What is claimed is:

1. An adhesive comprising a radiation cured silicone gel, wherein the silicone gel comprises a crosslinked poly diorganosiloxane material, a noncrossedlinked polydiorganosiloxane fluid, and a silicate resin tackifier.

2. The adhesive of claim 1, wherein the crosslinked poly diorganosiloxane material comprises a crosslinked poly dimethylsiloxane material and the noncrosslinked poly diorganosiloxane fluid comprises a noncrosslinked poly dimethylsiloxane fluid.

3. The adhesive of claim 2, wherein the poly dimethylsiloxane is selected from the group consisting of one or more silanol terminated poly dimethylsiloxanes, one or more nonfunctional poly dimethylsiloxanes, and combinations thereof 4. The adhesive of claim 2, wherein the poly dimethylsiloxane consists of one or more non-functional poly dimethylsiloxanes.

5. An adhesive comprising a radiation cured silicone gel, wherein the silicone gel comprises a crosslinked poly diorganosiloxane material and a poly(dimethylsiloxane-oxamide) linear copolymer.

6. The adhesive of claim 1, wherein the adhesive has a 180 degree peel adhesion from human skin of no greater than 200 grams per 2.54 centimeters as measured according to the Skin Peel Adhesion Procedure.

7. A medical article comprising a layer of the adhesive according to claim 1 adhered to a medical substrate.

8. The article of claim 7, wherein the layer has a thickness of 20 to 200 microns.

9. An adhesive formed by exposing a composition comprising a poly diorganosiloxane material to at least one of electron beam irradiation and gamma irradiation at a sufficient dose to crosslink the poly diorganosiloxane material and form a radiation cured silicone gel, wherein the silicone gel comprises a crosslinked poly diorganosiloxane material and a noncrosslinked polydiorganosiloxane fluid.

10. The adhesive of claim 9, wherein the crosslinked poly diorganosiloxane material comprises a crosslinked poly dimethylsiloxane material and the noncrosslinked poly diorganosiloxane fluid comprises a noncrosslinked poly dimethylsiloxane fluid.

11. The adhesive of claim 10, wherein the poly dimethylsiloxane is selected from the group consisting of one or more silanol terminated poly dimethylsiloxanes, one or more non-functional poly dimethylsiloxanes, and combinations thereof 12. The adhesive of claim 10, wherein the poly dimethylsiloxane consists of one or more non-functional poly dimethylsiloxanes.

13. An adhesive formed by exposing a composition comprising a poly diorganosiloxane material to at least one of electron beam irradiation and gamma irradiation at a sufficient dose to crosslink the poly diorganosiloxane material and form a radiation cured silicone gel, wherein the silicone gel comprises a crosslinked poly diorganosiloxane material and a poly(dimethylsiloxane-oxamide) linear copolymer.

14. The adhesive of claim 1, wherein the adhesive further comprises a hydrophilic polymer.

* * * * *

UNITED STATES PATENT AND TRADEMARK OFFICE
CERTIFICATE OF CORRECTION

| | |
|---|---|
| PATENT NO. | : 8,541,481 B2 |
| APPLICATION NO. | : 13/126346 |
| DATED | : September 24, 2013 |
| INVENTOR(S) | : Michael Determan |

It is certified that error appears in the above-identified patent and that said Letters Patent is hereby corrected as shown below:

<u>Title Page, Col. 1 (Related U.S. Application Data)</u>
Line 1                            Delete "Substitute for" and insert -- Provisional --, therefor.

<u>In the Drawings</u>
<u>Sheet 1 of 1 (FIG. 1)</u>
Line 4                            Below "120" insert -- FIG. 1 --.

<u>In the Specification</u>
<u>Column 1</u>
Line 60                         Delete "cloth," and insert -- cloth. --, therefor.

<u>Column 2</u>
Line 59                         Delete "polydimethysiloxane" and insert -- olydimethylsiloxane --, therefor.
Line 61                         Delete "tackifiying" and insert -- tackifying --, therefor.

<u>Column 4</u>
Line 28                         Delete "one is" and insert -- one in --, therefor.
Line 61                         Delete "50,000-gm/mole," and insert -- 50,000 gm/mole, --, therefor.

<u>Column 5</u>
Line 23                         Delete "polsiloxane" and insert -- polysiloxane --, therefor.

<u>Column 8</u>
Line 27                         Delete "a" and insert -- A --, therefor.

Signed and Sealed this
Eighteenth Day of November, 2014

Michelle K. Lee
*Deputy Director of the United States Patent and Trademark Office*

Column 11
Line 22          Delete "OHX-4070Terminal" and insert -- OHX-4070 Terminal --, therefor.
Line 23          Delete "tackifer" and insert -- tackifier --, therefor.

In the Claims
Column 12
Line 67          Claim 3, after "thereof" insert -- . --.